US006555731B2

(12) United States Patent
LaChapell et al.

(10) Patent No.: US 6,555,731 B2
(45) Date of Patent: Apr. 29, 2003

(54) PAD INTEGRITY IMPROVEMENT BY REPLACING THE CONSTRUCTIVE ADHESIVE WITH ULTRASONIC COMPRESSIONS

(75) Inventors: Ruth A. LaChapell, Menasha, WI (US); Chinmay S. Betrabet, Corvallis, OR (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 77 days.

(21) Appl. No.: 09/753,231

(22) Filed: Dec. 29, 2000

(65) Prior Publication Data

US 2002/0123725 A1 Sep. 5, 2002

(51) Int. Cl.$^7$ ................................................. A61F 13/15
(52) U.S. Cl. ...................... 604/379; 156/73.01; 156/91; 156/580.01; 604/385.01
(58) Field of Search ................................ 604/365, 380, 604/385.01, 378, 379; 128/885; 156/73.01, 91, 304.06, 580.01

(56) References Cited

U.S. PATENT DOCUMENTS

| 4,397,644 A | 8/1983 | Bornslaeger et al. |
| 4,443,512 A | 4/1984 | Delvaux |
| 4,650,481 A | 3/1987 | O'Connor et al. |
| 4,704,116 A | 11/1987 | Enloe |
| 4,761,322 A | 8/1988 | Raley |
| 4,823,783 A | 4/1989 | Willhite, Jr. et al. |
| 4,844,965 A | 7/1989 | Foxman |
| 4,886,697 A | 12/1989 | Perdelwitz, Jr. et al. |
| 4,939,017 A | 7/1990 | Foxman |
| 5,059,277 A | 10/1991 | Willhite, Jr. et al. |
| 5,128,193 A | 7/1992 | Nguyen et al. |
| 5,269,860 A | 12/1993 | Rice |
| 5,429,629 A | * 7/1995 | Latimer et al. ............. 604/378 |
| 5,599,338 A | 2/1997 | Enloe |
| 5,609,702 A | 3/1997 | Andersen |

FOREIGN PATENT DOCUMENTS

| CA | 1313923 | 3/1993 |
| EP | 0 438 113 | 7/1991 |
| EP | 0 589 222 | 3/1994 |
| GB | 2 279 229 | 4/1995 |
| GB | 2 283 700 | 5/1995 |
| GB | 2 281 212 | 2/1997 |
| WO | WO 95/235472 | 9/1995 |
| WO | WO 96/03951 | 2/1996 |
| WO | WO 99/25281 A | 5/1999 |

* cited by examiner

Primary Examiner—John J. Calvert
Assistant Examiner—Angela J. Grayson
(74) Attorney, Agent, or Firm—Kilpatrick Stockton LLP

(57) ABSTRACT

Disposable personal care products, such as diapers, feminine care products and adult incontinence products, are provided. More specifically, disposable personal care products having improved absorbent core integrity and core absorbency are provided. These products eliminate the need for costly adhesives. A method for making the products is also provided. The method includes forming a plurality of localized compressions by ultrasonically compressing the natural fiber core between, although not necessarily adjacent to, at least one upper and at least one underlying fusible material. The periphery of the article is then bonded by conventional means, such as adhesives, crimping or fusing. This process reduces costs associated with the manufacturing of such articles by eliminating or reducing the amount of adhesives in the final product, and by eliminating costly and intermittent bonding procedures. The method also improves the continuum of the absorbent core without increasing material and manufacturing costs associated with these products.

29 Claims, 4 Drawing Sheets

PAD INTEGRITY IMPROVEMENT BY REPLACING THE CONSTRUCTIVE ADHESIVE WITH ULTRASONIC COMPRESSIONS

FIELD OF THE INVENTION

The present invention relates to disposable personal care products, such as diapers, feminine care products and adult incontinence products. More specifically, the invention relates to products having improved absorbent core integrity, and methods for producing such products through ultrasonic compressions.

BACKGROUND OF THE INVENTION

Disposable care products are typically comprised of at least three general layers. These include an absorbent core placed between a liquid permeable inner liner and a liquid impermeable outer cover. The inner liner and outer cover can comprise one or more individual layers of materials, and additional layers can also be interposed between any of the general layers. For example, in the disposable diaper, the inner liner can comprise a surge layer consisting of thermoplastic fibers positioned beneath a thermoplastic mesh. Additionally, a tissue material, or wrap sheet, is often positioned between the outer cover and absorbent core, and between the surge layer and the absorbent core. At the diaper periphery, the material layers extending to the periphery are held together by conventional means, such as adhesives, crimping, fusing, or other methods known in the art.

The absorbent core receives and retains bodily fluids. It consists of a natural fiber batt that has a strong affinity for water and other hydrophilic components of bodily secretions. A dispersion of superabsorbent particles can also be incorporated into the fibrous core.

Maintaining a continuous, intact core, especially when these articles are used, is a recurring issue in the disposable garment industry. Breaks in the continuum of the core create open spaces that prevent the transport of fluid into the core, and the wicking of the fluid in the core. This breakdown of the core structure can cause fluids to leak out of the periphery of the diaper. The core breakdown also results in its sagging, which is visually unappealing to the consumer.

In the disposable diaper, adhesives used to bond various material interfaces within the diaper have not eliminated the breakdown of the absorbent core. The adhesive is conventionally applied in a swirl, spray or bead pattern between the outer cover and the wrap sheet, and/or between the surge layer and the wrap sheet. Moreover, adhesives placed between the wrap sheet and the inner liner reduce the absorbent property of the core by blocking the transport of fluids between these layers. The addition of an adhesive also increases the raw material costs associated with assembling disposable diapers. The standard adhesive loading is 0.31 to 0.33 grams of adhesive per diaper. Core integrity is not maintained at this loading. Additionally, it has been found that increasing the adhesive weight by tenfold, i.e., 3.1 to 3.3 grams per diaper does not appreciably improve core integrity.

Ultrasonically compressing the absorbent core between the inner liner and outer cover can be used in place of an adhesive to maintain the core integrity. Ultrasonic bonding involves high frequency mechanical energy transfers in the form of a reciprocating vertical motion. When ultrasonic energy is applied to several material layers, the vibrations within each material layer generate heat. Ultrasonic vibrations within a thermoplastic material will soften or melt the thermoplastic material if the heat generated increases the temperature of the thermoplastic material above the glass transition temperature or melting temperature, respectively. Thermoplastic materials are thus considered fusible.

The high crystallinity and high melting point of natural fibers makes these fibers infusible at the temperatures needed to soften or melt conventional thermoplastics. Since natural fibers are in general infusible, few attempts have been made to ultrasonically bond or weld a natural fiber core between two fusible materials. To ultrasonically bond a natural fiber core between two fusible materials, enough energy must be applied, and maintained within the layers, to fuse the fusible materials at the surface of the core, or to each other through the interstitial void volume in the core, without sufficiently deforming the fusible layers.

European Patent Application 0 438 113 A1 to S. J. Anapol et al. discloses an absorbent batt structure that has a discrete pattern of hydrogen bonded compressed portions formed on at least one surface of the batt. The batt contains fibers that are formed from a loose assemblage of cellulose, and, if needed, thermoplastic fibers, that has a discrete pattern of bonded compressed portions formed on at least one surface of the batt. These discrete compressions result in a batt structure with discrete density gradients, uniformly placed across the surface of the batt. These density gradients, in turn, result in enhanced fluid transfer between adjacent compressed portions, while substantially maintaining the absorbency of the batt. A water spray is applied to the surface of the batt and then an embossing roll, or ultrasonic energy, is applied to the surface to define a plurality of substantially, uniformly spaced, hydrogen-bonded compressed portions. Here, the core only is compressed and assembled into the final product, and a water spray is required to form the compressions in the core. Thus, a costly intermittent compression step is needed. The water spray may be needed to provide water molecules for hydrogen bond formation.

Other work involving absorbent articles disclose an actual fusion, or mechanical bonding of the material layers, as opposed to a pure compression of the these layers. For example, U.S. Pat. Nos. 4,823,783 and 5,059,277 to W. Willhite et al. disclose a method and apparatus for ultrasonically bonding continuous moving webs to one another using a stationary vibrating horn and a slick, thermally resistant slip layer. The slip layer is placed between the webs and the horns to prevent web damage. In this method, at least one of the webs to be bonded is comprised of a polymeric material which can be locally melted or softened by the input of mechanical energy. The slip layer maximizes heat retention in the web to be bonded, and ensures that neither the relatively delicate polymeric webs or the more resilient highly compressible webs are damaged in the bonding process. Two or more webs can be bonded together, but the protective slip layer is not bonded to the resultant laminate structure. The nature of the bond formed between one or more heat softened polymeric webs and other layers in the structure will vary depending on the chemical makeup of the other layers. If one or more layers does not soften by the input of mechanical energy, but exhibits significant interstitial void volume, the bonding will likely comprise mechanical entanglements of the melted or softened polymeric webs with the infusible web or webs, and/or the fusing of the polymeric webs to one another through the interstitial void volume in the infusible web.

U.S. Pat. Nos. 5,269,860 discloses the fusion of a thermoplastic sheet onto a thermoplastic or a non-thermoplastic fibrous textile. The thermoplastic sheet can be ultrasonically fused to a textile substrate that has an equivalent or higher melting temperature than the thermoplastic sheet. Ultrasonic energy is applied to the thermoplastic sheet, and the sheet melts before the textile surface begins to soften. This results in a fusion between the melted thermoplastic and the textile fibers. The ultrasonic energy can be applied to localized sections of the thermoplastic sheet to form various patterns of the fused thermoplastic sheet and fiber substrate. U.S. Pat. No. 5,609,702 to V. E. Andersen discloses a method for mutually bonding at least two moving continuous webs to form a laminate containing at least one puckered material layer. These webs can be bonded by thermal or ultrasonic techniques. At least one of the webs comprises weldable material; however, the preferred approach is to bond webs, each containing a weldable material.

Other work in the area of articles containing an absorbent core have combined natural fibers with heat-fusible thermoplastic fibers, or other polymer additives, to improve the fusion and compression of the core. The application of thermal or ultrasonic energy to the combined core, or to substrates adjacent to the core, thermally fuses the thermoplastic material present in the core to other fibers within the core, and to other thermoplastic materials at the interface of the core, respectively. However, the inclusion of hydrophobic thermoplastic materials in the core within the voids and interstitial spaces reduces moisture intake and rate of wicking. Moreover, the addition of thermoplastic fibers to a natural fiber core adds additional expense to the fabrication of the disposable product. Examples of such systems of the prior art are disclosed in U.S. Pat. No. 4,886,697 to L. E. Perdelwitz, et al.; U.S. Pat. Nos. 4,844,965 and 4,939,017 to C. Foxman; and International Patent Application WO 98/27904 to K. S. Lynard et al.

Thus, there is a need for disposable diapers having improved absorbent core integrity upon wear, while maintaining the absorption capacity of the natural fiber core.

There is also a need to reduce costs in the manufacturing of these articles by eliminating or reducing the amount of adhesives in the final product, and by eliminating costly and intermittent bonding procedures.

Therefore, there is a need in the art to improve the continum of the absorbent core without increasing material and manufacturing costs associated with these products.

There is also a need to eliminate additional material components, such as adhesives, and intermittent bonding procedures.

Further, there is also a need to maintain the core absorbency of the intact core in terms of the amount of fluid intake and its retention.

SUMMARY OF THE INVENTION

The present invention is directed to disposable care products that, upon use, maintain a better core integrity and absorption and methods for their production. These products eliminate the need for additional material components, such as adhesives, and intermittent bonding procedures. Further, these products maintain the core absorbency of the intact core in terms of the amount of fluid intake and its retention.

In one aspect, the present invention comprises a disposable personal care product having improved absorbent core integrity upon wear. The product comprises a liquid permeable inner liner, a liquid impermeable outer, a natural fiber core positioned between the inner liner and outer cover, and a region containing a plurality of localized compressions formed by ultrasonically compressing the natural fiber core between, although not necessarily adjacent to, at least one upper and at least one underlying fusible material.

In another aspect, the present invention comprises a method of making a disposable personal care article having improved absorbent core integrity upon wear. The method comprises positioning a natural fiber core between, but not necessarily adjacent to, a liquid permeable inner liner and a liquid impermeable outer cover. Next, a region containing a plurality of localized compressions is formed by ultrasonically compressing the natural fiber core between, although not necessarily adjacent to, at least one upper and at least one underlying fusible material. The periphery of the article is then bonded by conventional means, such as adhesives, crimping or fusing.

This process reduces costs associated with the manufacturing of such articles by eliminating or reducing the amount of adhesives in the final product, and by eliminating costly and intermittent bonding procedures. The method also improves the continuum of the absorbent core without increasing material and manufacturing costs associated with these products.

Thus, it is an object of the present invention to provide disposable personal care products having improved absorbent core integrity upon wear while maintaining the absorption capacity of the core.

It is another object of the invention to provide disposable personal care products having improved absorbent core integrity upon wear, containing a natural fibrous core that is ultrasonically compressed between at least one upper and at least one underlying fusible material.

It is yet another object of the present invention to provide disposable personal care products having improved absorbent core integrity upon wear that do not contain an adhesive at the inner planar surface, as opposed to the edges, of any material layer.

It is an object of the present invention to provide a method of making disposable personal care products having improved absorbent core integrity upon wear while maintaining the absorption capacity of the core.

It is another object of the invention to provide a method of making disposable personal care products having improved absorbent core integrity upon wear, containing a natural fibrous core that is ultrasonically compressed between at least one upper and at least one underlying fusible material.

It is yet another object of the present invention to provide a method of making disposable personal care products having improved absorbent core integrity upon wear that do not contain an adhesive at the inner planar surface, as opposed to the edges, of any material layer.

It is a further object of the present invention to provide a method of making disposable personal care products having improved absorbent core integrity upon wear by ultrasonically compressing, in one step, the natural fiber absorbent core between at least one upper and at least one underlying fusible material.

It is an object of the present invention to provide a method of making disposable personal care products having improved absorbent core integrity upon wear by ultrasonically compressing, in one step, the natural fiber absorbent core between at least one upper and at least one underlying fusible material, and applying the ultrasonic energy to only one of the fusible materials.

It is another object of the present invention to provide a method of making disposable personal care products having improved absorbent core integrity upon wear, by ultrasonically compressing, in one step, the natural fiber absorbent core between at least one upper and at least one underlying fusible material, and applying the ultrasonic energy to only one of the fusible materials after the assembly of all the product's material layers.

These and other objects of the present invention will be more readily apparent when considered in reference with the following description.

BRIEF DESCRIPTION OF THE DRAWINGS

This patent contains at least one color photograph. Copies of this patent with the color photographs will be provided by the Patent & Trademark Office upon request and payment of the necessary fee.

DETAILED DESCRIPTION OF THE INVENTION

Figure 1:
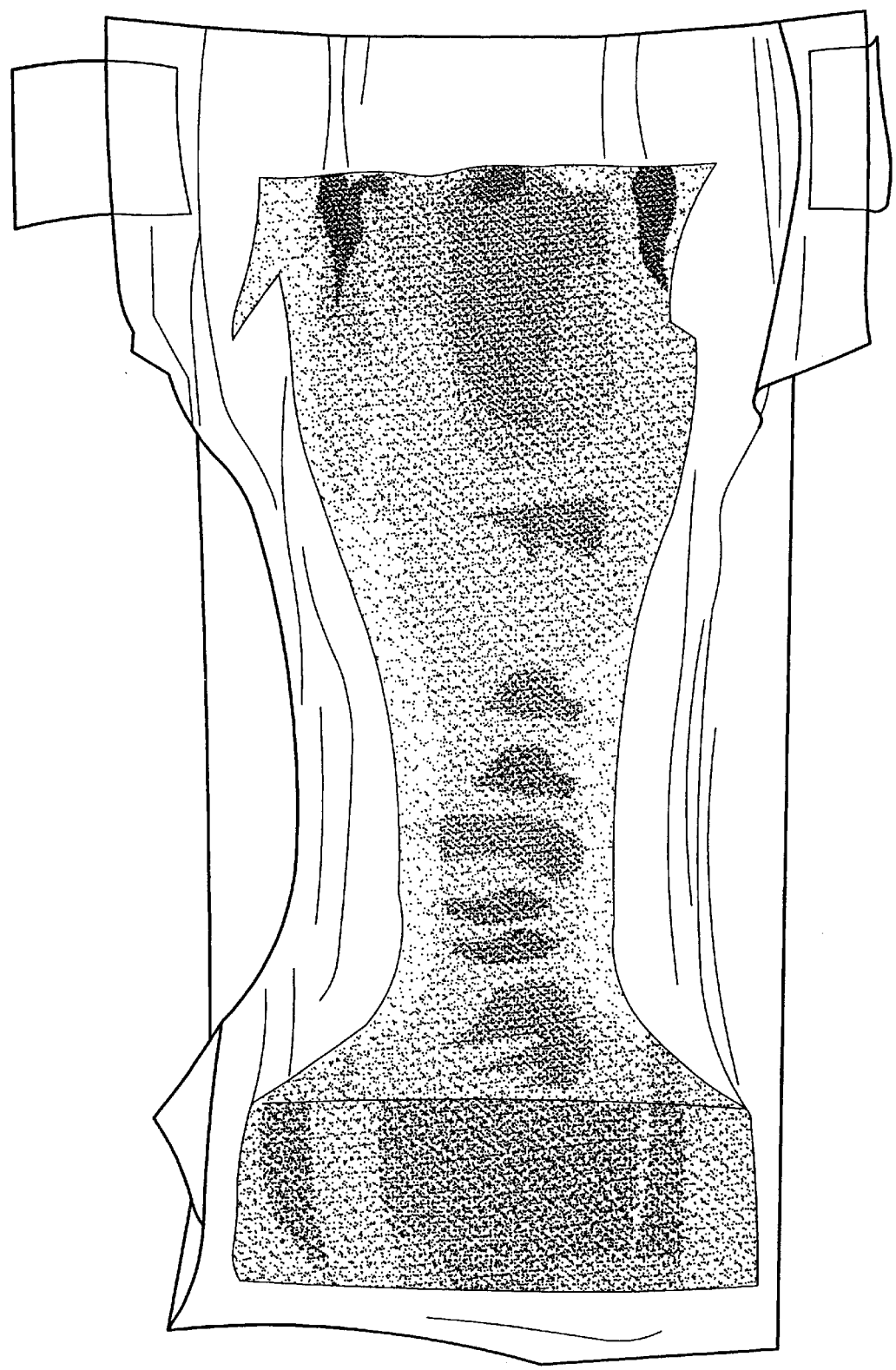
FIG. 1 shows an intact diaper core in form of a light box.

The present invention comprises disposable, personal care products that, upon use, maintain a better core integrity and absorption than conventional products. Such products include, but are not limited to, diapers, training pants, feminine care products, and incontinence products.

Generally, personal care products of the invention comprise three or more layers of synthetic and natural materials. These layers include a liquid permeable inner liner, an absorbent core, and a liquid impermeable outer cover. The absorbent core is positioned between the inner liner and outer cover.

The inner liner can be manufactured from a wide range of materials, such as woven and nonwoven polymeric fibers or a combination of synthetic and natural fibers. Typical polymeric fibers include polyethylene, polypropylene and polyester fibers. Typical natural fibers include cellulose, wood pulp and cotton.

The outer impermeable cover in one instance comprises a multilayered polymer films, nonwovens, laminates of films and nonwovens, laminates of nets and films, laminates of nets and nonwovens of polyethylene, polypropylene, polyesters, polyvinyl alcohols, and polyvinyl acetates. In another instance, the outer cover comprises a composite material, such as a film-coated nonwoven material.

The absorbent core comprises natural fibers, such as cellulose, wood pulp, or cotton. The core has a strong affinity for water and other hydrophilic components of bodily secretions. The absorbent core can take any form suitable for use in absorbent composites. For example, the core can be in the form of a natural fiber batt or regenerated cellulose and can contain a dispersion of superabsorbent particles. Other forms of superabsorbent materials include, but are not limited to, fibers, flakes, spheres, films, foams, sprays, and printable superabsorbent materials.

The inner liner and outer cover can comprise one or more individual layers of materials. For example, the inner liner may comprise a surge layer containing, for example, thermoplastic fibers positioned beneath a thermoplastic mesh. Further, additional layers can be interposed between any of the three general layers. For example, an inner tissue material or wrap sheet is optionally positioned between the outer cover and absorbent core, and between the surge layer and the absorbent core.

The natural fiber core of the present invention can be heated and compressed between two fusible materials using ultrasonic energy without forming an ultrasonic bond or weld and without significantly deforming the fusible materials. It may also be possible to form compressions using sufficient localized pressure in the absence of ultrasonic energy.

Ultrasonic compressions are employed to provide improved contact between the layers of the article. This contact occurs without bonding the fusible materials to the natural fiber core, or to one another. The compression sites are used in place of an ultrasonic bond to keep the natural fiber core in place and serve to reduce the break-up of the absorbent core, thus maintaining the absorption capacity of the core. While the use of ultrasonic compressions are preferred, other methods of forming the compressions are contemplated by the invention. Such methods include the use of air or hydraulic pressure.

In particular, ultrasonic energy can be applied to either the inner liner or outer cover of the article or both. Ultrasonic energy involves high frequency mechanical energy in the form of a reciprocating vertical motion. Such ultrasonic energy applied to thermoplastic materials results in a softening or melting of the thermoplastic if the heat generated increases the temperature of the thermoplastic above the glass transition temperature or melting temperature. In contrast, the high crystallinity and high melting point of the natural fibers used in the absorbent core of the present invention makes the core infusible at the temperatures needed to soften or melt conventional thermoplastics.

The compressions eliminate the need for an adhesive between the material layers of the article. The compressions can be done during assembly of the article, or can be done as a one-step process after complete assembly of all the article layers, eliminating intermittent bonding procedures and saving manufacturing time and expense. The compressions can be applied to either the inner liner or outer cover of the article. The compressions can be formed at discrete locations within the surge area of the diaper and can be prepared manually using a hand-held bonder, or in a continuous fashion on a rotary bonder.

The ultrasonic compressions, extending within the unexposed fibrous layer of the absorbent core anchor the core fibers between compression sites. In addition, the compressions act as stress points, absorbing a higher shear force, as opposed to uncompressed core, before breaking apart. Thus, these ultrasonic compressions help to reduced breaks in the continuum of the absorbent core, and this, in turn, reduces the amount of void space within the core, and the amount of fluid accumulating in the void spaces and leaking out of the periphery of the article. This is especially beneficial when the article is a diaper.

Although the scope of the invention encompasses any type of disposable personal care product, the invention will be further illustrated with regard to diapers. It will be understood by one skilled in the art that the following discussion would also apply to other types of personal care products and in no way limits the scope of the invention.

The present application teaches that the ultrasonic compression of a natural fiber core between at least one upper and at least one underlying fusible material serves to maintain the core's integrity and absorption properties when the diaper is in use. The ultrasonic compressions can replace costly adhesives and other costly bonding procedures. Moreover, the ultrasonic compressions can be formed after the product is completely assembled.

Moreover, the surface area of each compression can be small enough so that total surface area of all of the compressions comprises only a small percentage of the total surface area of the absorbent core. For example in this invention, the total area of the compressions comprises about 1.5% of the total area of the absorbent core, spread out, for example, in a pattern of 10×10, 35×40, or 20×20. This small area of compression helps to maintain the absorbent properties of the core by maximizing the amount of core fibers free to absorb and wick fluids. Finally, the compressions can be used in place of an adhesive, and thus eliminate the problems associated with the adhesive blocking the passage of fluids into the core.

Although these compression sites can be formed in one step, that is by one application of ultrasonic energy to the surface of a fusible material, after the product is completely assembled, the compression sites are generally formed during intermediate steps in the diaper assembly process so that the material layers are bonded together as individual components and then introduced to the product line.

This invention is further illustrated by the following examples, which are not to be construed in any way as imposing limitations upon the scope thereof. To the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1
Preparation of the Ultrasonic Bonds

Ultrasonic compressions were preformed on six, size 3, test diapers. Each diaper consisted of a liqiud impervious backsheet, a cellulose pulp absorbent core, and a nonwoven thermoplastic fibrous inner liner. The cellulose core contained a dispersion of superabsorbent particles. No adhesive was applied between any of the material layers in these diapers. The diapers were processed on a standard diaper machine. All material layers were assembled together and bonded only at the perimeter of each diaper using conventional means. The perimeter bonding did not come in contact with the absorbent core. Ultrasonic compressions were then applied to the surge area of the assembled diapers.

A hand-held, plunge bonder from Sonics & Materials, Inc., model HSM 3, was used to ultrasonically compress the test diapers. The bonder was powered by a 2000 Auto-Trac (20 KHz, 2000 Watt) ultrasonic generator from Dukane Corporation. The bonder also contained a rectangular slotted horn and a dot-pattern anvil design. The horn, manufactured by Branson Ultrasonics Corporation, had dimensions of 0.5" depth×6.0" wide×5.5" high. The bonder was equiped with an oblong tip, 4 ½ mm in length and 1 ½ mm in width. The bonder, operating at a power setting of "five," efficiently locally compressed the inner liner, absorbent core and outer cover together without burning any of the material layers, or poking holes through these layers. During the compression process, each diaper remained stationary by firm, hand-held pressure.

The ultrasonic compressions were placed in the surge area of each diaper, where the absorbent core breaks apart more extensively. To identify any performance differences resulting from the direction the ultrasonic energy was applied, compressions were delivered to either the inner liner or the outer cover for each test diaper. Compressions were placed at three different spacing within the surge area: 35 mm×45 mm, 20 mm×20 mm, and 10 mm×10 mm.

The integrity of the absorbent core in the test diapers was compared against two controls. In one control, an adhesive bonded the outer cover to a wrap sheet, placed between the absorbent core and the outer cover. The adhesive add-on (loading) on the coversheet or outer liner was approximately 0.3 gram adhesive per diaper spread uniformly using a swirl pattern. In the second control, no adhesive or any other bonding mechanism, was used to hold the material layers together, other than the bonding at the diaper periphery. The core integrity of each diaper was evaluated using a "high kick" test described below.

Example 2
Evaluation of Core Integrity

Figure 2:
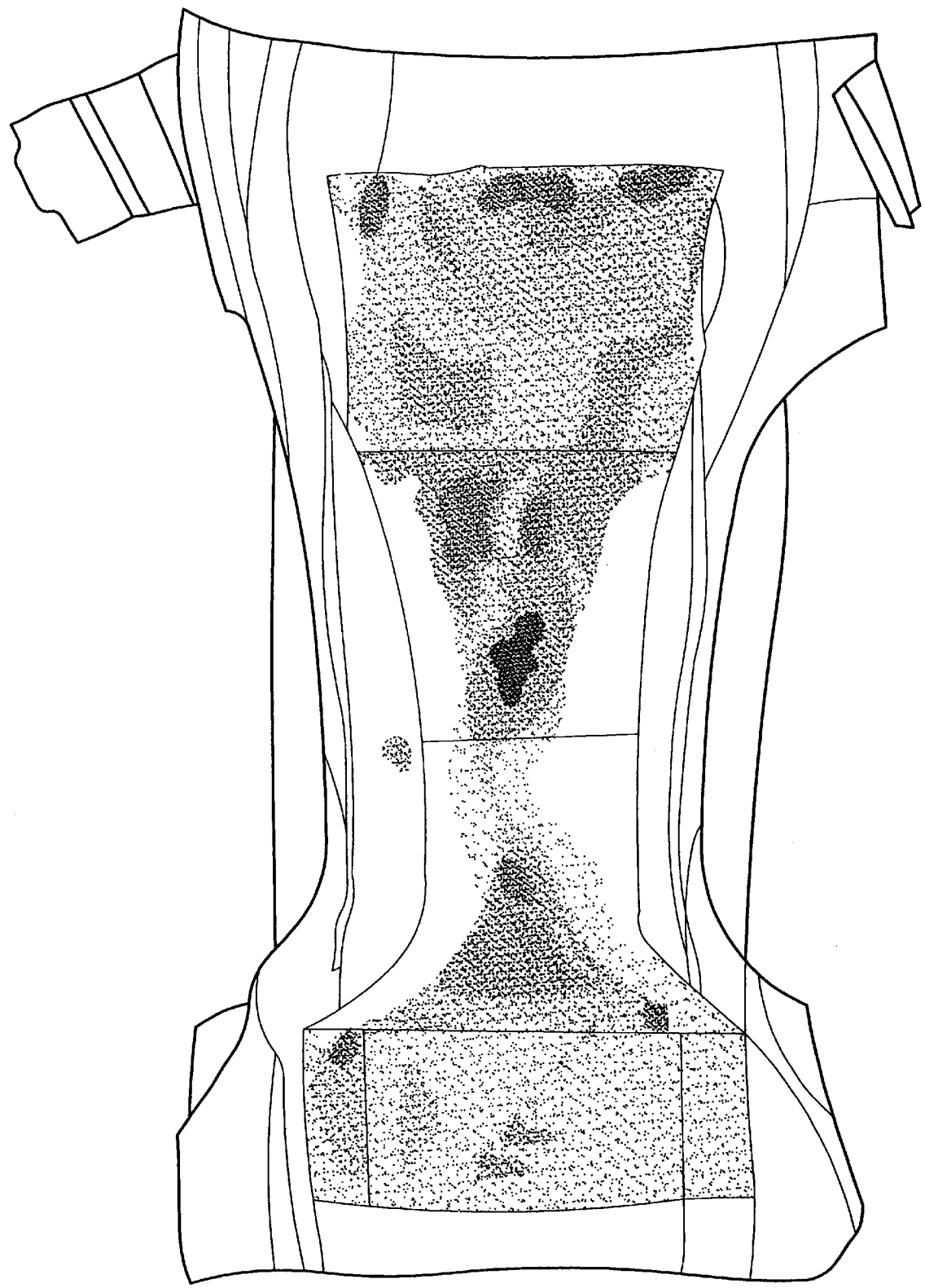
FIG. 2 shows the diaper core control having "no adhesive" in front of a light box after 120 minutes of the high kick test.
Figure 3:
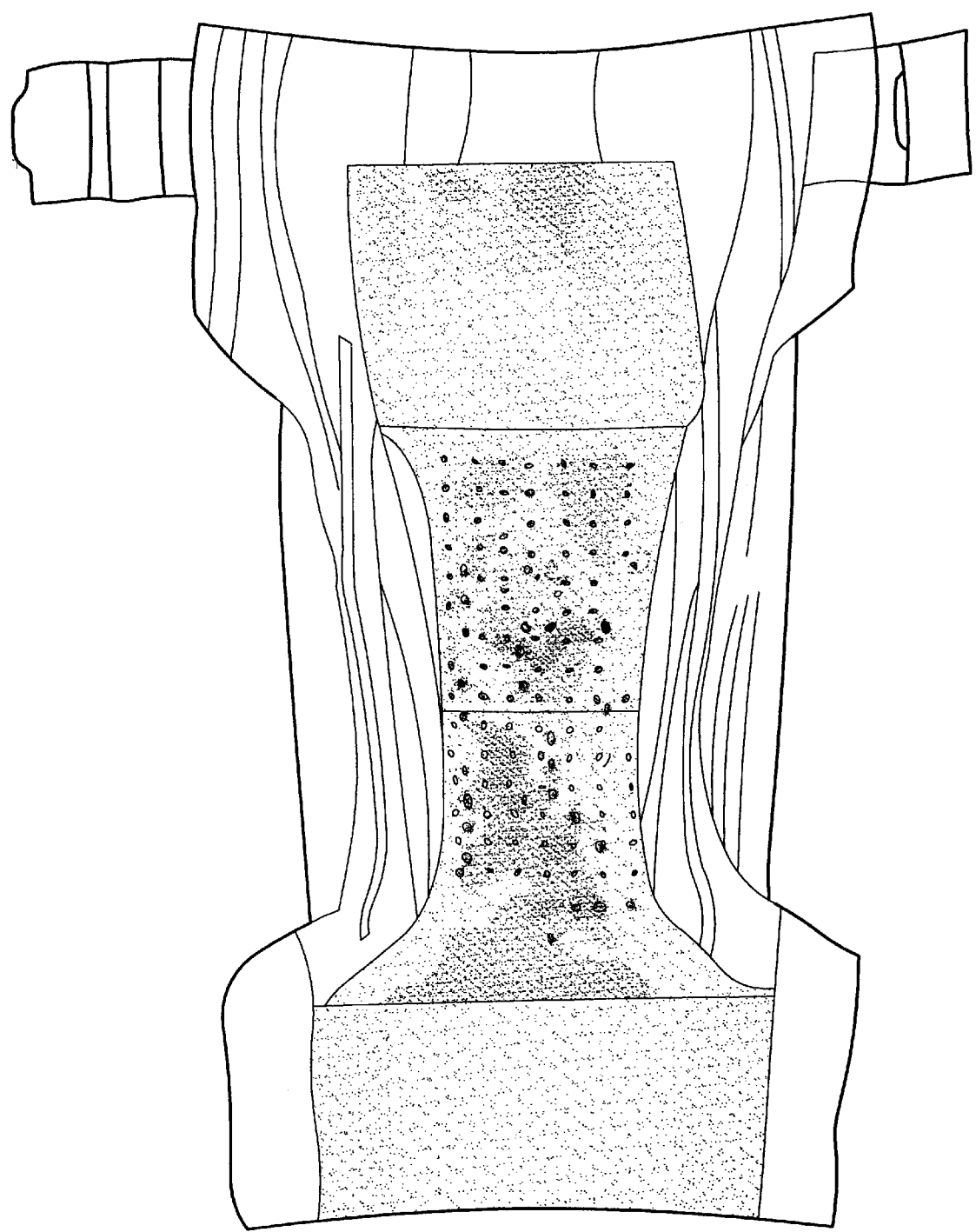
FIG. 3 shows the 10 mm×10 mm compression patterned inner liner test diaper in front of a light box after 120 minutes of the high kick test.
Figure 4:
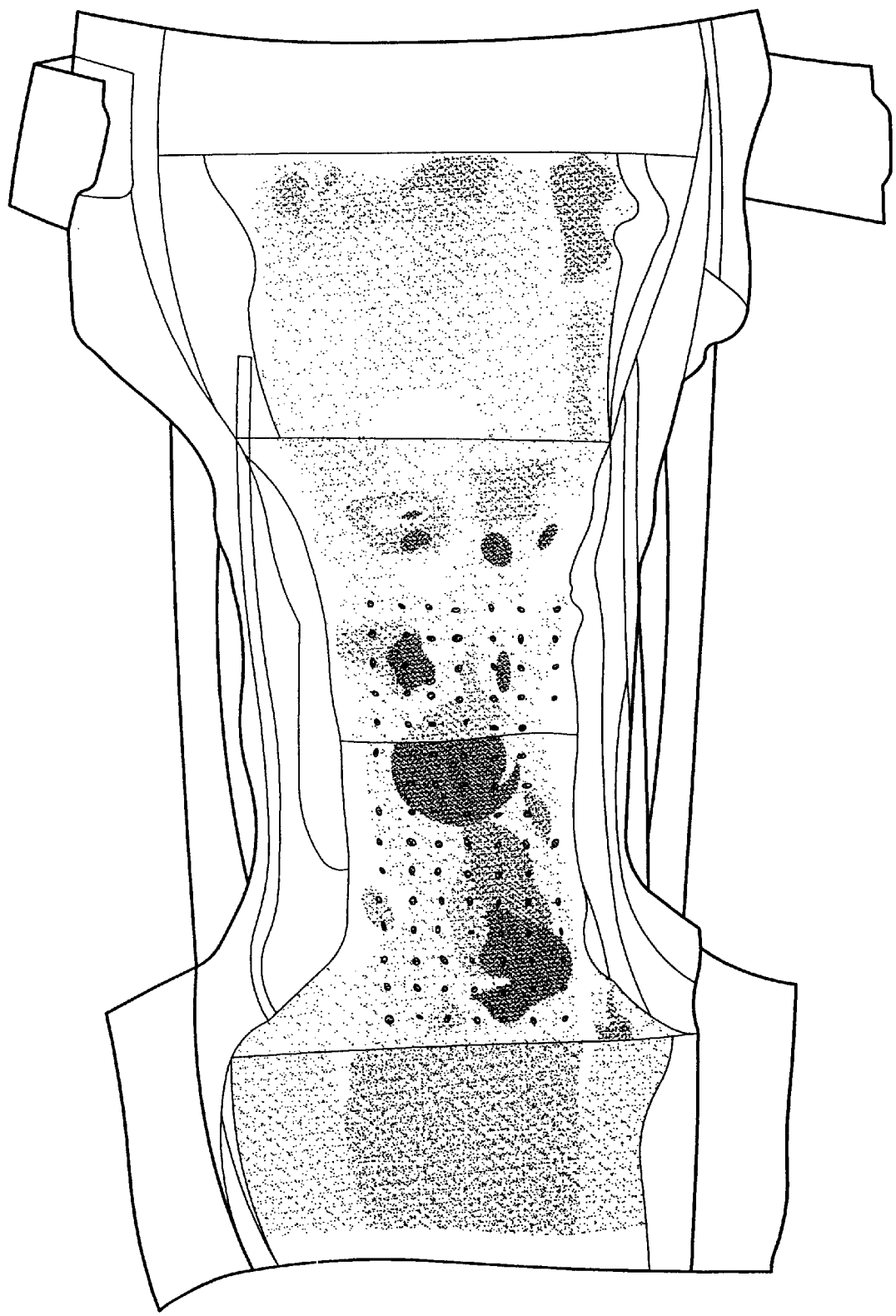
FIG. 4 shows the 10 mm×10 mm compression patterned outer cover test diaper in front of a light box after 120 minutes of the high kick test.

The core integrity of each diaper was evaluated using a "High Kicking Baby Model." This model simulates the high kick of an active child. Each kick is approximately 60° to 90° from floor level. Each diaper, in the dry state, was tested on this high kick model for a total of 120 minutes. The dry diaper, high kick test represents the worst case scenario for absorbent core break-up. The integrity of the diaper core was analyzed at the following time points: 10, 20, 30, 60, 90 and 120 minutes. The core integrity was analyzed by stretching each diaper along its longitudinal axis in front of a light box, with the inner liner facing the light. Each diaper was stretched to its full length and place against the surface of the light box. Two clips mounted to the glass surface of the light box held the top end of the diaper, containing the side adhesive tabs, in place. Two weights were placed at the opposite end of the diaper to stretch the diaper, and hold it in place. Prior to subjecting a diaper to the high kick test, the diaper was stretched out before the light box, and the perimeter of the intack absorbent core was traced with a permanent ink marker. The enclosed area served as a reference from which future measurements were compared. The enclosed core area in an untested diaper averaged around 22,500 square millimeter, and encompassed the entire range of the absorbent core, from the front to the back of the diaper. FIG. 1 shows an intack diaper core in front of the light box. At each time interval during the "high kick" test, each diaper was examined in front of the light box, and the approximate void space, or total area separation, within the absorbent core, measured. FIGS. 2 and 3 show the "no-adhesive" control after 120 minutes, and the 10 mm×10 mm, inner liner test diaper after 120 minutes, respectively. The lighter regions, where the background light transmitted, denoted the voids or separation within the absorbent core. The darker regions, where the background light scattered, represented intack core. The end results of the kick test are shown in Table 1. Tables 2 and 3 list the total area of separation at each time point for the ultrasonic energy delivered to the inner liner and outer cover, respectively.

TABLE 1

Core Integrity After 120 Minutes on the High Kicking Baby Model
Total Area Separated (sq. mm)/% Area Separated

| Control (Adhesive) | Control (No Adhesive) | Ultrasonic Compressions (mm × mm) | | |
|---|---|---|---|---|
| | | 35 × 40 | 20 × 20 | 10 × 10 |
| 5445/24% | 6060/27% | 2021/9%[a] | 2056/9%[a] | 319/2%[a] |
| | | 3141/14%[b] | 2239/10%[b] | 1117/5%[b] |

[a] ultrasonic bond delivered to inner liner
[b] ultrasonic bond delivered to outer cover

TABLE 2

Core Integrity During the High Kicking Baby Model
Ultrasonic Compressions Delivered to Inner Liner
Total Area Separated (sq. mm)/% Area Separated

| Time (min) | CONTROLS | | ULTRASONIC SPACING (mm × mm) | | |
|---|---|---|---|---|---|
| | Adhesive | No Adhesive | 35 × 40 | 20 × 20 | 10 × 10 |
| 10 | 1505/7% | 1874/8% | 216/1% | 93/1% | 100/1% |
| 20 | 2694/12% | 2784/12% | 320/2% | 612/2% | 106/1% |
| 30 | 3014/13% | 3756/17% | 710/3% | 828/3% | 160/1% |
| 60 | 3487/16% | 5303/24% | 790/4% | 1747/4% | 240/1% |
| 90 | 4980/22% | 5520/25% | 1522/7% | 1959/7% | 285/1% |
| 120 | 5445/24% | 6060/27% | 2021/9% | 2056/9% | 319/2% |

TABLE 3

Core Integrity During the High Kicking Baby Model
Ultrasonic Compressions Delivered to Outer Cover
Total Area Separated (sq. mm)/% Area Separated

| Time (min) | CONTROLS | | ULTRASONIC SPACING (mm × mm) | | |
|---|---|---|---|---|---|
| | Adhesive | No Adhesive | 35 × 40 | 20 × 20 | 10 × 10 |
| 10 | 1505/7% | 1874/8% | 409/2% | 0/0% | 397/2% |
| 20 | 2694/12% | 2784/12% | 753/3% | 561/3% | 511/2% |
| 30 | 3014/13% | 3756/17% | 1527/7% | 738/4% | 638/3% |
| 60 | 3487/16% | 5303/24% | 2184/10% | 1721/8% | 743/3% |
| 90 | 4980/22% | 5520/25% | 2609/12% | 2035/9% | 959/4% |
| 120 | 5445/24% | 6060/27% | 3141/14% | 2239/10% | 1117/5% |

The data clearly shows that the break-up the core structure significantly decreased in the test diapers containing the ultrasonic compressions as opposed to the control diapers. The integrity of the core also improves when the ultrasonic compressions are spaced closer together. A slight improvement is observed when the ultrasonic energy is applied to the inner liner as opposed to the outer cover. Also, only minimal improvement in core integrity is observed when the constructive adhesive is used as opposed to no adhesive. These results verify the conclusion that the ultrasonic compressions are anchoring the core between compression sites, and also serving as stress points, absorbing a higher shear force, before breaking apart. The improved core continuum maintains the core's absorbent properties and thus reduces the amount of leakage of fluids out of the periphery of the diaper. In this invention, the area of compression comprised about 1.5% of the total area of the absorbent core. This small area of compression sites helps to maintain the absorbent properties of the core by maximizing the amount of core fibers free to absorb and wick fluids. In addition, the elimination of any adhesive reduces the risk that the adhesive blocks the passage of fluids into the absorbent core.

The above description is intended to be illustrated and not restrictive. While particular embodiments of the present invention have been illustrated and described, it would be obvious to those skilled in the art that various other changes and modifications can be made without departing from the spirit and scope of the invention.

What is claimed:

1. A method of making a disposable personal care article having improved absorbent core integrity upon wear, said method comprising:
    (a) positioning a natural fiber core between, but not necessarily adjacent to, a liquid permeable inner liner and a liquid impermeable outer cover;
    (b) forming a region containing a plurality of localized compressions by ultrasonically compressing the natural fiber core between, although not necessarily adjacent to, at least one upper and at least one underlying fusible material; and
    (c) bonding the periphery of the article by conventional means.

2. The method of claim 1, wherein the inner liner wholly or partially comprises a thermoplastic material.

3. The method of claim 2, wherein the inner liner comprises polyethylene, polypropylene or polyester, or a combination thereof.

4. The method of claim 3, wherein the inner liner further comprises cellulose, wood pulp, cotton, or a combination thereof.

5. The method of claim 1, wherein the outer cover wholly or partially comprises a thermoplastic material.

6. The method of claim 5, wherein the outer cover comprises a polyethylene-polypropylene laminate.

7. The method of claim 6, wherein the outer cover further comprises a film-coated nonwoven material.

8. The method of claim 1, wherein the natural fiber core comprises cellulose, wood pulp, cotton, or any combination thereof.

9. The method of claim 8, wherein the natural fiber core contains a dispersion of superabsorbent particles, fibers, flakes, spheres, foams, sprays, or printable superabsorbent.

10. The method of claim 1, wherein no adhesive is placed at the inner planar surface of any of the material layers, other than at the periphery of the diaper.

11. The method of claim 1, wherein the natural fiber core is ultrasonically compressed, in one step, between at least one upper and at least one underlying fusible material.

12. The method of claim 11, wherein the natural fiber core is ultrasonically compressed, in one step, between at least one upper and at least one underlying fusible material, by applying ultrasonic energy to the exposed surface of the inner liner.

13. The method of claim 12, wherein the ultrasonic energy is applied to the exposed surface of the inner liner after the assembly of the diaper's material layers.

14. The method of claim 11, wherein the natural fiber core is ultrasonically compressed, in one step, between at least one upper and at least one underlying fusible material, by applying ultrasonic energy to the exposed surface of the outer cover.

15. The method of claim 14, wherein the ultrasonic energy is applied to the exposed surface of the outer cover after the assembly of the diaper's material layers.

16. The method of claim 1, wherein the area of the compression sites comprise less than 2% of the total area of the absorbent core.

17. A disposable personal care article having improved absorbent core integrity upon wear, comprising:
    (a) a liquid permeable inner liner;
    (b) a liquid impermeable outer;

(c) a natural fiber core positioned between the inner liner and outer cover; and (d) a region containing a plurality of localized compressions formed by ultrasonically compressing the natural fiber core between, although not necessarily adjacent to, at least one upper and at least one underlying fusible material.

18. The article of claim 17, wherein the inner liner wholly or partially comprises a thermoplastic material.

19. The article of claim 18, wherein the inner liner comprises polyethylene, polypropylene, polyester, or a combination thereof.

20. The article of claim 19, wherein the inner liner further comprises cellulose, wood pulp, cotton, or a combination thereof.

21. The article of claim 17, wherein the outer cover wholly or partially comprises a thermoplastic material.

22. The article of claim 21, wherein the outer cover comprises a polyethylene-polypropylene laminate.

23. The article of claim 21, wherein the inner liner further comprises a film-coated nonwoven material.

24. The article of claim 17, wherein the natural fiber core comprises cellulose, wood pulp, cotton, or any combination thereof.

25. The article of claim 24, wherein the natural fiber core comprises a dispersion of superabsorbent particles, fibers, flakes, spheres, foams, sprays, or printable superabsorbents.

26. The article of claim 17, wherein no adhesive is placed at the inner planar surface of any of the material layers, other than at the periphery of the diaper.

27. The article of claim 17, wherein the natural fiber core is ultrasonically compressed, in one step, between at least one upper and at least one underlying fusible material.

28. The article of claim 17, wherein the area of the compression sites comprise less than 5% of the total area of the absorbent core.

29. The article of claim 28, wherein the area of the compression sites comprise less than 2% of the total area of the absorbent core.

* * * * *